United States Patent
Cummins et al.

(10) Patent No.: US 10,154,919 B2
(45) Date of Patent: Dec. 18, 2018

(54) PULL WIRE AND SPOOL FOR VASCULAR INTERVENTION DEVICE DELIVERY SYSTEM

(71) Applicant: Cook Medical Technologies LLC, Bloomington, IN (US)

(72) Inventors: Sean Cummins, Limerick (IE); Darach McGrath, Tipperary (IE)

(73) Assignee: Cook Medical Technologies LLC, Bloomington, IN (US)

( * ) Notice: Subject to any disclaimer, the term of this patent is extended or adjusted under 35 U.S.C. 154(b) by 316 days.

(21) Appl. No.: 14/837,510

(22) Filed: Aug. 27, 2015

(65) Prior Publication Data
US 2016/0074194 A1 Mar. 17, 2016

Related U.S. Application Data

(60) Provisional application No. 62/050,388, filed on Sep. 15, 2014.

(51) Int. Cl.
*A61F 2/966* (2013.01)
*A61F 2/95* (2013.01)
(Continued)

(52) U.S. Cl.
CPC ............... *A61F 2/95* (2013.01); *A61F 2/844* (2013.01); *A61F 2/962* (2013.01); *A61F 2/966* (2013.01);
(Continued)

(58) Field of Classification Search
CPC ............ A61F 2/013; A61F 2/95–2/97; A61F 2/2427–2/2439
(Continued)

(56) References Cited

U.S. PATENT DOCUMENTS 1,392,321 A * 10/1921 Gammeter ............. B65H 75/28
242/587.1
2,151,837 A * 3/1939 Burke ..................... B66D 1/34
14/21
(Continued)

FOREIGN PATENT DOCUMENTS

| EP | 2431009 | 3/2012 |
| WO | 2008034793 | 3/2008 |

OTHER PUBLICATIONS

Information Disclosure Statement and Declaration of Darach McGrath Re: ev3 Inc. Stent Delivery System On-Sale Jul. 11, 2013 Prior Art.

*Primary Examiner* — Kathleen Holwerda
(74) *Attorney, Agent, or Firm* — Liell & McNeil

(57) ABSTRACT

A vascular intervention device delivery system, such as for implanting a self expanding stent, includes a thumbwheel rotatably mounted in a handle. The thumbwheel includes a radially outward thumb surface and a spool. A catheter has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. The pull terminates at a proximal end with an integral anchor that extends through an opening in a wall that separates an inner surface of spool from a collection surface. The retractable sheath moves responsive to rotation of the thumbwheel in a first direction.

19 Claims, 4 Drawing Sheets

(51) Int. Cl.
*A61F 2/962* (2013.01)
*A61F 2/844* (2013.01)
*A61B 17/00* (2006.01)

(52) U.S. Cl.
CPC ........... *A61B 2017/00407* (2013.01); *A61F 2002/9517* (2013.01); *A61F 2230/0069* (2013.01)

(58) Field of Classification Search
USPC .................................. 242/579–587.3, 118.3
See application file for complete search history.

(56) References Cited

U.S. PATENT DOCUMENTS

| | | | |
|---|---|---|---|
| 2,652,918 A * | 9/1953 | Lippert | B41J 33/006 242/587.1 |
| 2,653,775 A * | 9/1953 | Eastman | G03B 21/326 242/586.2 |
| 3,802,638 A * | 4/1974 | Dragan | B41J 33/006 242/586.2 |
| 5,707,376 A * | 1/1998 | Kavteladze | A61F 2/90 623/1.11 |
| 6,146,338 A * | 11/2000 | Gardeski | A61M 25/0138 600/585 |
| 6,190,360 B1 | 2/2001 | Iancea et al. | |
| 6,238,402 B1 | 5/2001 | Sullivan, III et al. | |
| 7,614,439 B2 * | 11/2009 | Lukos | E04F 10/0633 160/310 |
| 7,967,829 B2 | 6/2011 | Gunderson et al. | |
| 7,976,574 B2 | 7/2011 | Papp | |
| 8,500,789 B2 | 8/2013 | Wuebbeling et al. | |
| 2005/0080476 A1 * | 4/2005 | Gunderson | A61F 2/95 623/1.11 |
| 2005/0103921 A1 * | 5/2005 | Winter | B66D 1/34 242/587.1 |
| 2005/0149159 A1 | 7/2005 | Andreas et al. | |
| 2005/0273151 A1 | 12/2005 | Fulkerson et al. | |
| 2006/0259124 A1 * | 11/2006 | Matsuoka | A61F 2/966 623/1.12 |
| 2007/0032860 A1 | 2/2007 | Brooks et al. | |
| 2007/0055342 A1 | 3/2007 | Wu et al. | |
| 2007/0060999 A1 * | 3/2007 | Randall | A61F 2/95 623/1.11 |
| 2007/0088421 A1 | 4/2007 | Loewen | |
| 2007/0156225 A1 | 7/2007 | George et al. | |
| 2007/0168014 A1 | 7/2007 | Jimenez et al. | |
| 2008/0091257 A1 | 4/2008 | Andreas et al. | |
| 2009/0210046 A1 | 8/2009 | Shumer et al. | |
| 2010/0004606 A1 | 1/2010 | Hansen et al. | |
| 2012/0041537 A1 | 2/2012 | Parker et al. | |
| 2012/0059448 A1 | 3/2012 | Parker et al. | |
| 2012/0101562 A1 | 4/2012 | Gunderson et al. | |
| 2012/0123516 A1 | 5/2012 | Gerdts et al. | |
| 2012/0158120 A1 | 6/2012 | Hacker et al. | |
| 2012/0330401 A1 | 12/2012 | Sugimoto et al. | |
| 2013/0013047 A1 | 1/2013 | Ramos et al. | |
| 2013/0018451 A1 | 1/2013 | Grabowski et al. | |
| 2013/0110223 A1 | 5/2013 | Munsinger et al. | |
| 2014/0188209 A1 | 7/2014 | Loewen | |
| 2015/0297378 A1 * | 10/2015 | Senness | A61F 2/95 623/1.11 |

* cited by examiner

PULL WIRE AND SPOOL FOR VASCULAR INTERVENTION DEVICE DELIVERY SYSTEM

TECHNICAL FIELD

The present disclosure relates generally to vascular intervention device delivery systems, and more particularly to a pull wire and spool for a thumbwheel actuated vascular intervention device delivery system.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficulty maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent. Another potential concern relates to creation of a robust and repeatable terminal connection between a pull wire and take up spool for thumbwheel actuated delivery systems.

The present disclosure is directed toward one or more of the problems set forth above.

SUMMARY OF THE DISCLOSURE

A vascular intervention device delivery system includes a thumbwheel rotatably mounted in a handle, and having a radially outward thumb surface and a spool. A catheter has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. The spool has inner surface separated from a collection surface by a wall, and the pull terminates at a proximal end with an integral anchor that extends through an opening in the wall and contacts the inner surface. The retractable sheath moves responsive to rotation of the thumb wheel in a first direction.

DETAILED DESCRIPTION

Figure 1:
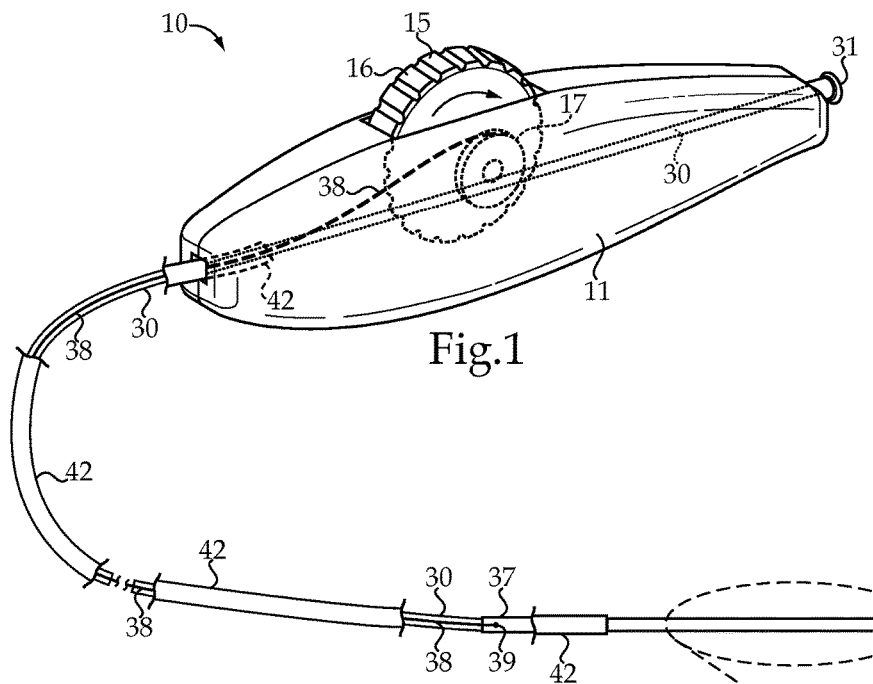
FIG. 1 is a perspective schematic view of a vascular intervention device delivery system according to the present disclosure.
Figure 2:
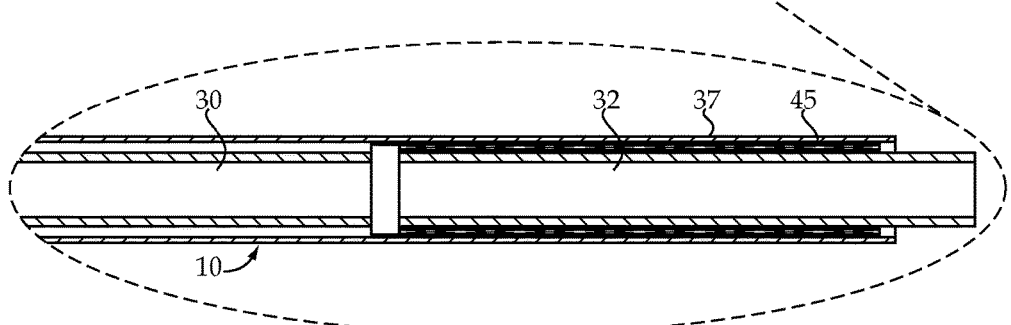
FIG. 2 is an enlarged view of the distal segment of the delivery system shown outlined with a dashed line in FIG. 1.
Figure 3:
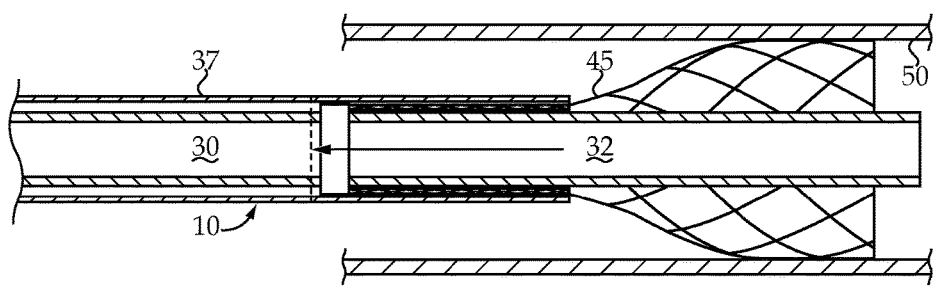
FIG. 3 is a view similar to FIG. 2 about half way through a deployment of a self expanding stent.

Referring to FIGS. 1-3, a vascular intervention device delivery system 10 is shown before and during delivery of a self expanding stent 45 into the vessel 50 of a patient. Delivery system 10 includes a handle 11 that may be gripped in one hand by a user during a delivery procedure. Handle 11 may, for instance, be manufactured from a suitable molded plastic, such as in two longitudinal halves that are joined in any suitable manner to form the complete handle 11. A thumbwheel 15 is rotatably mounted in the handle 11 and has a radially outward thumb surface 16 and a spool 17. A catheter 30 has a proximal end 31 attached to handle 11, and a distal carrier segment 32 for mounting a vascular intervention device, such as a self expanding stent 45, thereon. Proximal end 31 may take the form a Luer lock fitting to receive a guide wire or so that treatment fluids or the like may be injected through catheter 30 in a manner well known in the art. A retractable sheath 37 is movable with respect to catheter 30 from a first position covering the distal carrier segment 32 to a second position indicated by the dashed line in FIG. 3 at which the retractable sheath 37 has been retracted proximally to uncover the distal carrier segment 32. FIG. 3 shows the retractable sheath 37 about half way between the first position and the second position.

A pull 38 extends between the spool 17 of thumbwheel 15 and the retractable sheath 37. Pull 38, which preferably is less elastic than the retractable sheath 37, may be attached to retractable sheath 37 at an attachment 39 in any manner known in the art, such as by welding pull 38 to a metallic reinforcement of retractable sheath 37. In some versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic wire or thin band of metal. For instance, pull 38 could take the form of a band of spring steel (thickness less than width) having a curved cross section.

A wire retention/stability sheath 42 surrounds a majority of the length of pull 38, and serves to keep pull 38 in close proximity to the outer surface of catheter 30 over much of the length of delivery system 10. Wire retention/stability sheath 42 may be unattached to catheter 30, pull 38 or retractable sheath 37, but may be attached to move with pull 38 and/or retractable sheath 37. On the other hand, wire retention/stability sheath 42 may be attached to catheter 30 at one or more locations so that pull 38 and retractable sheath 37 also move with respect to wire retention/stability sheath 42 during the delivery process. In the illustrated embodiments, retention/stability sheath 42 is connected at its proximal end to handle 11. Thus, wire retention/stability sheath 42 may terminate and be attached at its proximal end at a fixation point within handle 11.

When in its pre-deployment configuration, as shown in FIGS. 1 and 2, a vascular intervention device, such as a self expanding stent 45, is disposed between an outer surface of the distal carrier segment 32 of catheter 30, and an inner surface of the retractable sheath 37. During a typical procedure, the distal carrier segment 32 is positioned at a treatment location within a vessel 50 of a patient. After achieving proper positioning, the user then grips handle 11 and begins to rotate thumbwheel 15 so that pull 38 is wound onto spool 17. As this occurs, pull 38 and retractable sheath 37 move proximally with respect to catheter 30 to allow the self expanding stent 45 to expand away from carrier segment 32 and into contact with the inner wall of vessel 50 in a manner well known in the art. During this process, catheter 30 is placed in compression while both pull 38 and retractable sheath 37 are in tension. According to the present disclosure, handle 11 and thumbwheel 15 may include a structure that allows thumbwheel 16 to rotate to wind pull 38 onto spool 17, but prevent rotation in an opposite direction. This aspect of the disclosure allows the user to stop the deployment procedure while retaining the stored elastic energy in pull 38 and retractable sheath 37.

Figure 4:
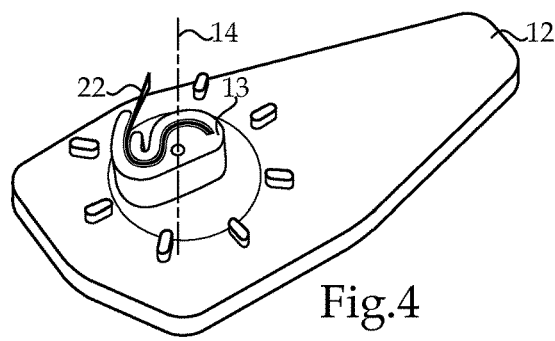
FIG. 4 is a perspective view of an assembly plate for the handle shown in FIG. 1.
Figure 5:
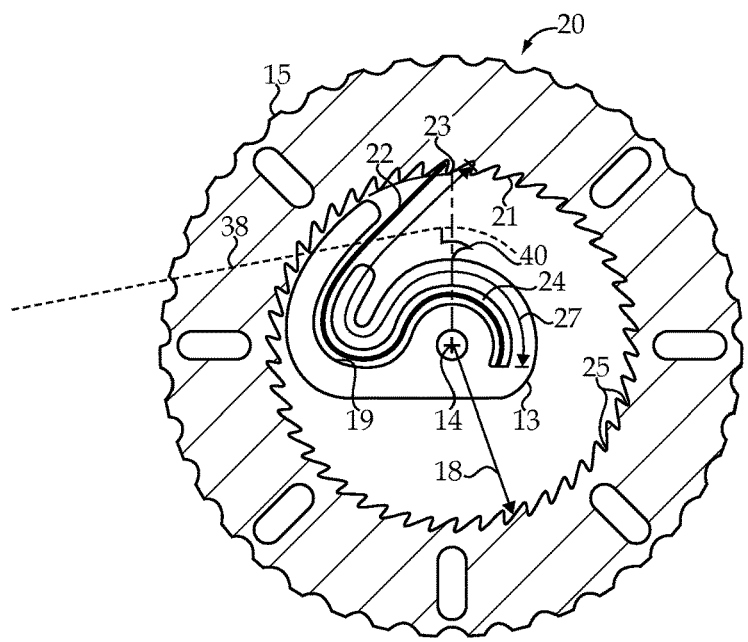
FIG. 5 is a partial sectioned view showing the ratchet according to the present disclosure.
Figure 6:
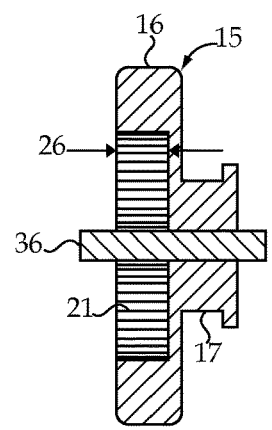
FIG. 6 is a sectioned side view through the thumbwheel of FIGS. 1 and 5.

Referring now in addition to FIGS. 4-6, a ratchet 20 provides the structure that prevents thumbwheel 16 from rotating in a forward direction. In particular, handle 11 may be formed to include, or have attached to an inner surface, an assembly plate 12 that defines a hub 13 that receives an axle 36 upon which thumbwheel 16 is rotatably mounted to rotate about axis 14 in a reverse direction permitted by ratchet 20. Thumbwheel 15 includes a radially inward ratchet surface 31 of ratchet 20. A ratchet pawl 22 of ratchet 20 is mounted in the handle 11, and has a catch 23 in contact with ratchet surface 21 of thumbwheel 15. Ratchet 20 holds thumbwheel 15 against rotation in a forward direction, but the retractable sheath 37 moves responsive to rotation of the thumbwheel 15 in a reverse direction.

In the illustrated embodiment, catch 23 takes the form of a deformed rectangular shaped band of spring steel 24 that is received in an S-shaped groove 19 defined by assembly plate 12 and oriented parallel to axis 14. The ratchet surface 21 of thumbwheel 15 may define a plurality of stops 25 in each of four 90° rotation angles. In the specific embodiment shown, ratchet surface 21 defines at least fifty stops 25 per revolution of thumbwheel 15 in order to provide the user with precise tactile control over the delivery procedure. The deformed band of spring steel 24 may have a width that contacts the ratchet surface 21 across the width 26. In addition, although not necessary, the deformed band of spring steel 24 may have a length 27 that is greater than radius 18 of thumbwheel 15. An imaginary line 40 that extends parallel from an end 28 of catch 23 to the axis 14 may be configured to be orthogonal to pull 38 where pull 38 contacts spool 37, as best shown in FIG. 5.

Referring now to FIGS. 7-12, a vascular intervention device delivery system 60 according to another aspect may include a ratchet 70 and a handle 61 with a structure that differs from that shown in relation to FIGS. 4-6. However, where similar numbers are used, those features correspond to similar features shown in FIGS. 1-3. Vascular intervention device delivery system 60 differs from the system 10 described earlier by the shape and structure of the ratchet pawl 72 and by the inclusion of a lock 80. Like the earlier version, ratchet 70 may provide a structure that prevents thumbwheel 66 from rotating in a forward direction.

Handle 61 may be formed from a suitable plastic to include a key shaped hub 62 that is received in a matching key shaped opening 74 defined by ratchet pawl 72. This configuration permits assembly of ratchet pawl 72 to key shaped hub 62 in a plurality of different but equivalent angular orientations. Key shaped hub 72 may define a central opening that receives an axle 63 to define an axis 64 about which thumbwheel 65 rotates. Thumbwheel 65 includes a radially outward thumb surface 66 and a radially inward ratchet surface 71. Thumbwheel 65 may also include a spool 67 upon which the pull 38 is wound when the device delivery system 60 is operated. In this version, the wire retention/stability sheath 42 terminates at a junction box 43 (not shown in FIG. 7 for the sake of clarity) positioned within handle 61. As in the previous version, the pull 38 is positioned within the wire retention/stability sheath 42 and emerges from the junction box 43 to wrap around an idler wheel 44 and return in the reverse direction for being wound onto spool 67 as best shown in FIGS. 7, 8, 11 and 12. As in the previous embodiment, ratchet 70 prevents thumbwheel 65 from rotating in a forward direction, but the retractable sheath 37 (FIGS. 1-3) moves responsive to rotation of thumbwheel 65 in a reverse direction.

In this embodiment, catch 73 takes the form of spiral arms 79 that are attached to a central body 76 by living hinges 77. Unlike the ratchet pawl 22 shown in the embodiment in FIGS. 4-6, ratchet pawl 72 may most conveniently be formed of a suitable plastic material. When thumbwheel 65 is rotated in a reverse direction, each of the three catches 73 will click and be received into respective stops 75 that define ratchet surface 71. In this embodiment, ratchet catches 73 are equally distributed 120° apart around the axis 64 defined by axle 63. Thus, the three catches 73 will simultaneously contact the ratchet surface 71 at three different locations located 120° apart about axis 64. Those skilled in the art will appreciate that a ratchet pawl 72 having two, four or more catches 73 would also fall within the intended scope of this disclosure.

Figure 7:
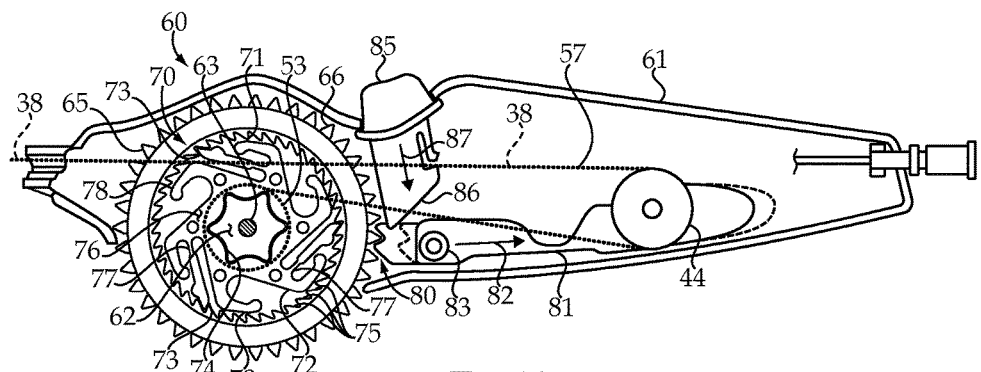
FIG. 7 is a sectioned side view of a handle portion of a vascular intervention device delivery system according to another aspect of the present disclosure.
Figure 8:
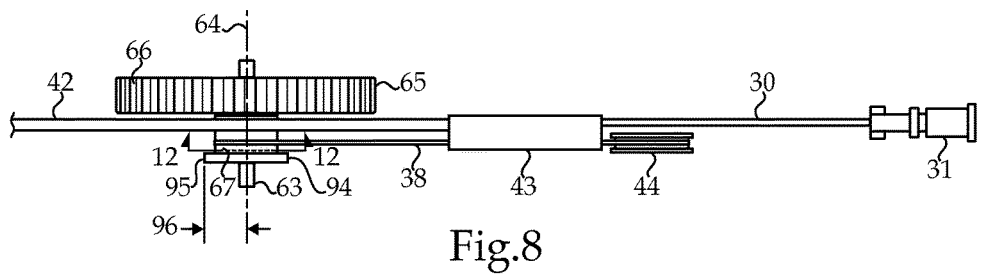
FIG. 8 is a top view of the inner workings of the vascular intervention device delivery system of FIG. 7, minus the handle.
Figure 9:
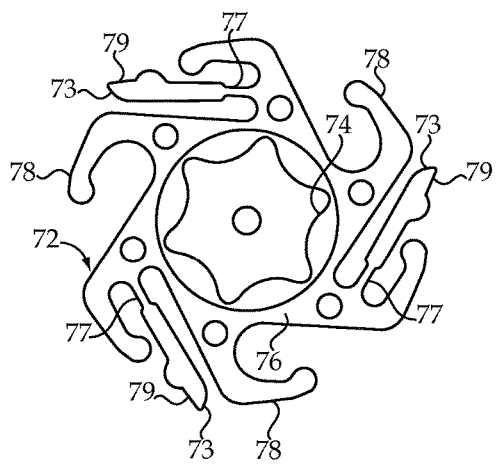
FIG. 9 is a side view of a ratchet pawl for the vascular intervention device delivery system of FIG. 7.

As best shown in FIGS. 7 and 9, the ratchet pawl 72 includes curved arms 78 that are distributed to provide a circular guide for the thumbwheel as the ratchet teeth rotate around the fixed ratchet. Thus, in some embodiments, the use of curved arms 78 could permit omission of axle 63 as shown, since the thumbwheel would rotate about axis 64 with the curved arms 78 contacting ratchet surface 71, even without the inclusion of axle 63. It is also worth noting that this embodiment differs from the earlier embodiment in that both the ratchet pawl 72 and the ratchet surface 71 of thumbwheel 65 may be made out of plastic, as opposed to a metal ratchet pawl 22 acting on a plastic ratchet surface 21 as in the earlier embodiment. By making both the pawl and the ratchet surface from the same material, the potential creation of the debris caused by the interaction of metal with plastic can be avoided.

In addition to ratchet 70, vascular intervention device delivery system 60 may include a lock 80 that allows thumbwheel 65 to be disabled during shipment and during positioning of the distal carrier segment 32 (FIGS. 1-3) at a treatment location within a patient. The lock 80 is movable between a locked position, as shown, and an unlocked position shown by dashed lines. The lock 80 includes a latch 81 positioned in handle 61 and movable along a line 82 between the locked position at which the latch 81 engages the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a wedge 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

Figure 10:
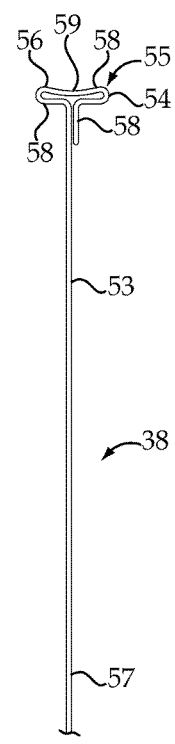
FIG. 10 is a side view of a portion of a pull for the vascular intervention delivery system of the present disclosure.
Figure 11:
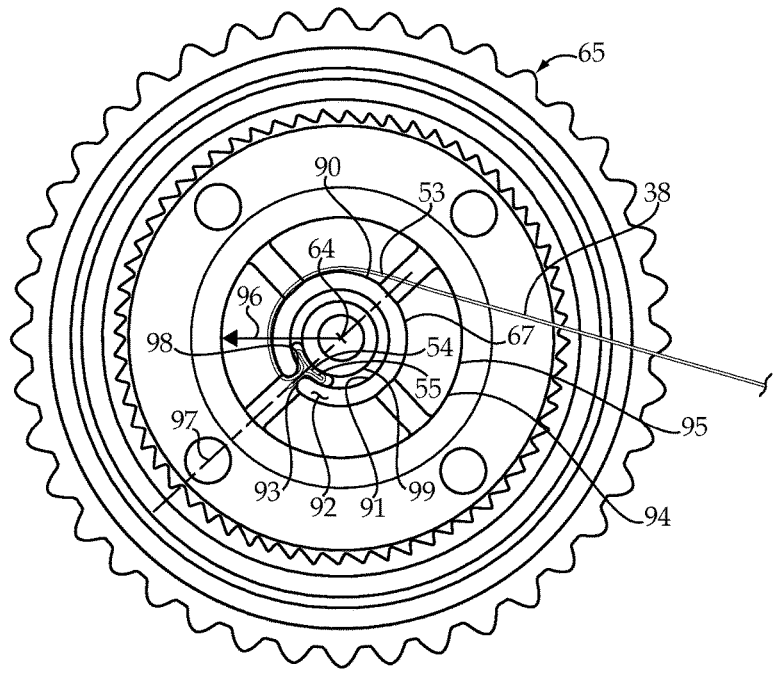
FIG. 11 is a side view of the pull of FIG. 10 partially wound onto a spool for the thumbwheel of FIG. 7.
Figure 12:
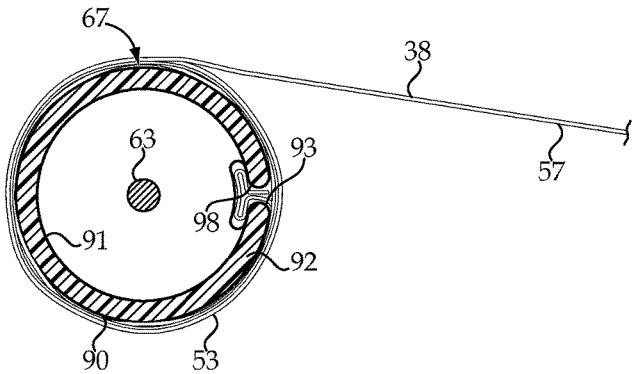
FIG. 12 is a sectioned side view of the spool of FIG. 8 as viewed along section lines 12-12 of FIG. 8.

Referring now more specifically to FIGS. 10-12, pull 38 is shown taking the form of a relatively thin band of spring steel with a curved cross section. Preferably, pull 38 is one integral length from its distal attachment point 39 to a proximal end 54 that is connected to spool 37. Pull 38 may have a majority of its length biased toward a straight configuration. In order to form proximal end 54 with an integral anchor 55, a proximal segment 53 of pull 38 may be annealed to provide greater ductility than a distal segment 57, which may comprise a majority of the length of pull 38. As used in the present disclosure, the term "integral" means that the identified features originate from the same part. Thus, integral anchor 55 is merely a deformed segment of the pull 38 and was never detached therefrom. An integral anchor 55 according to the present disclosure has never been separated from a remaining portion of pull 38, and then attached by some means such as a weld or adhesives or the like. Although integral anchor 55 could be formed on an un-annealed proximal segment 53 of pull 38, there are at least two reasons to consider annealing proximal segment 53 in order to increase ductility relative to the distal segment 57. First, forming un-annealed spring steel into the profile shape (T-shape) 56 can potentially result in breakage or substantial cracking at the severe bends where the wire band is bent back upon itself. Secondly, the best results have been observed when the vascular intervention device delivery system is initially manufactured, stored prior to use, and during an initial use maneuvering to the desired implantation site by having the pull 38 wound at least one time and maybe as many as three to four times around the collection surface 90 of spool 67. In other words, proximal segment 53 may be wound at least once completely around collection surface 90 when the retractable sheath is at its first position covering the self expanding stent 45. The greater ductility of the proximal section 53 not only helps in the forming of the integral anchor 55 without cracking or breakage, but also better facilitates the initial winding of pull 38 onto spool 67.

In the illustrated example, the integral anchor 54 has a T-shape 56 in which each of three legs 58 of the T-shape 56 is defined by two side by side segments of the pull 38. The top 59 of the T-shape 56 may be concave to match an outer radius of axle hub outer surface 99. The spool 67 defines a T-shaped slot 98 that is sized to received the T-shape 56 of the integral anchor 55. T-shaped slot 98, which may also include a top concave shape, opens in a direction parallel to axis 64. After passing through the T-shaped slot 98, the integral anchor 55 is positioned to extend through an opening 93 in a wall 92 that separates an inner surface 91 from collection surface 90 of spool 67. Thus, the integral anchor 55 will contact the inner surface 91, and extend through the opening 93, which may have a centerline 97 that intersects axis 64.

Spool 67 may include a rim 94 in order to help inhibit wound segments of pull 38 from sliding off of collection surface 90. Rim 94 includes an outer rim surface 95 that is a rim radius 96 from axis 64. The portion of pull 38 that is wound around collection surface 90 is less that the rim radius 96 from axis 64. Collection surface 90 may have a width that is about twice a width of pull 38. The term about twice means that the ratio of widths is two when rounded to one significant digit. This aspect of the disclosure helps to inhibit slippage in pull 38 that could result from a less tight winding of pull 38 around spool 67. Preferably, pull 38 is contact wound around collection surface 90 as best shown in FIG. 12. As used in the present disclosure, the term "contact wound" means that each winding of the pull 38 is either in contact with collection surface 90 or in contact with a previous winding of pull 38 around contact surface 90. Although the illustrated embodiment shows the proximal end 54 of pull 38 terminating in a T-shaped 56 integral anchor 55, those skilled in the art will appreciate that other integral anchor shapes could be utilized without departing from the present disclosure. For instance, an integral anchor according to the present disclosure will always include bends in the pull 38 that result in enlarged portions extending above and below a thickness profile of pull 38. In the illustrated example, the two top legs 58 of the T-shape 56 meet this requirement. However, those skilled in the art will appreciate that numerous other integral anchor shapes, including asymmetrical shapes, would also fall within the intended scope of the present disclosure. Some of these alternatives might require a different shaped slot from T-shaped slot 98 or may require no slot. Provided that the anchor is integral, these other alternatives as would occur to persons with ordinary skill would also fall within the intended scope of this disclosure. Thus, other alternative anchor shapes could fit in the annular space between the inner surface 91 and the axle hub outer surface 99.

In the illustrated embodiment, one might anneal a proximal segment 53 on the order of 30-40 millimeters in length, and form the integral anchor 55 out of maybe 10-15 millimeters of that proximal segment 53. The remaining portion of the proximal segment 53, and maybe some of the distal segment 57 may be wound onto spool 67 at the time of assembly and manufacture when retractable sheath 37 is still at its distal first position. By manufacturing with the expectation that at least one and maybe as many as three or four windings will begin on spool 67 when retractable sheath 67 is still in its first position, tight tolerances on a precise length for pull 38 are not necessary. Furthermore, tight tolerances with regard to what length of the pull 38 is consumed in order to form integral anchor 55 are also relaxed because of the initial windings on spool 67. This relaxation of dimensional length tolerances with regard to pull 38 not only reduces potential scrap, but also provides for a more robust design that arrives ready for use with little to no slack in pull 38 when the deployment procedure begins.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site. Finally, the present disclosure is specifically applicable to a manufacturing strategy that is robust, repeatable and reliably couples the pull 38 to the spool 67.

The vascular intervention device delivery system 10, 60 will typically be packaged in a conventional sterile packaging in a known manner for shipment. After a wire guide (not shown) has been positioned in a patient's body across a treatment location, the catheter 30 may be slid over the wire guide to position the distal carrier segment 32 and the attached self expanding stent 45 at the treatment location within the vessel 50 of the patient. Thereafter, the wire guide may be withdrawn or left in place. During this portion of the procedure, the thumbwheel 65 of the vascular intervention device delivery system 60 may be disabled by maintaining the lock 80 in its locked position as shown in FIG. 7. Recalling, while still locked, there may be at least one and as many as three or four complete windings of pull 38 on spool 67. After the distal carrier segment 32 is properly positioned and it is now time to deploy the self expanding stent 45, the user may depress pusher 85 to disengage lock 80 and move latch 81 out of contact with the radially outward thumb surface 66 of thumbwheel 65.

A method of operating vascular intervention device delivery system 10, 60 includes rotating the thumbwheel 15, 65 in a reverse direction to wind pull 38 further onto spool 17, 67 to build up tension in the retractable sheath 37 and pull 38 without moving the retractable sheath 37 relative to the distal carrier segment 32 of catheter 30. The "reverse direction" is clockwise for the embodiment of FIG. 1 and counterclockwise for the embodiment of FIG. 7. Next, a portion, which is less than all, of the distal carrier segment 32 is uncovered by continuing to rotate the thumbwheel 15, 65 in the reverse direction. At some point during the delivery procedure, the user may then pause rotation of the thumbwheel 15, 65 in the reverse direction. For instance, the user may pause in order to confirm that the vascular intervention device, such as a self expanding stent 45, is being delivered to the desired location in the vessel 50 of the patient. While the rotation of the thumbwheel 15, 65 is paused, tension in the pull 38 and the retractable sheath 37 is maintained by holding the ratchet 20, 70 and preventing rotation of the thumbwheel 15, 65 in the forward direction. Ratchet 20, 70 may be considered to be in a hold configuration when catches 23, 73 are received in one of the stops 25, 75 of the ratchet surface 21, 71. A remaining portion of the distal carrier segment 32 is then uncovered to facilitate complete deployment of the self expanding stent 45 by resuming rotation of the thumbwheel 15, 65 in the reverse direction until retractable sheath 37 arrives at its second position fully uncovering distal carrier segment 32.

One aspect of the ratchet operated vascular intervention device delivery system 10, 60 of the present disclosure is to allow for rotation of thumbwheel 15, 65 in one direction only. This means that the pull 38 and hence the retractable sheath 37 can only be pulled proximally. If the thumbwheel 15, 65 were able to rotate in both directions, it could cause the pull 38 to slack and possibly jump out of the collection diameter of the spool 17, 67 on thumbwheel 15, 65. Also, by keeping the rotation of thumbwheel 15, 65 to one direction only, ratchet 20, 70 allows all of the energy already placed in the system 10, 60 by the user to be maintained. For example, if the user was to partially deploy a self expanding stent 45 that had a deployment force of 30 N they will have to put effort into getting the stent to partially deploy. This effort could have caused the sheath 37 to stretch slightly and also the inner catheter 30 to compress slightly. If this energy were lost when the thumbwheel 15, 65 were released, it would mean that when the deployment was resumed from that point, the user would have to rotate the thumbwheel 15, 65 an amount in order to reestablish tension in the system 10, 60 again before the self expanding stent 45 would continue to deploy. This may be especially important in the case of deploying longer stents that require higher forces.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A vascular intervention device delivery system comprising:
    a handle that defines a central opening with a center that defines an axis of rotation;
    a thumbwheel that includes an axle received in the central opening so that the thumbwheel is rotatably mounted in the handle to rotate about the axis of rotation, and having a radially outward thumb surface and a spool;
    a catheter with a proximal end attached to the handle, and a distal carrier segment for mounting a vascular intervention device thereon;
    a retractable sheath movable from a first position covering the distal carrier segment to a second position retracted proximally uncovering the distal carrier segment;
    a pull extending between the thumbwheel and the retractable sheath, and including a distal segment extending distally beyond a distal end of the handle;
    wherein the spool has an inner surface separated from a collection surface by a wall, and the pull extends through a wall opening in the wall and terminates at a proximal end with an integral anchor that is a deformed segment of the pull in contact with the inner surface;
    the retractable sheath moving responsive to rotation of the thumbwheel in a first direction; and
    wherein the pull is wound at least once completely around the collection surface when the retractable sheath is at the first position.

2. The vascular intervention device delivery system of claim 1 wherein the pull includes a proximal segment integral with the distal segment;
    the proximal segment includes the integral anchor; and
    the proximal segment has a greater ductility than the distal segment.

3. The vascular intervention device delivery system of claim 2 wherein the spool rotates about the axis of rotation with the thumbwheel;
    the spool has a rim with an outer rim surface that is a rim radius from the axis, and the collection surface is positioned between the thumbwheel and the rim; and
    a portion of the pull that is wound around the collection surface is less than the rim radius from the axis.

4. The vascular intervention device delivery system of claim 3 wherein the pull is contact wound around the collection surface.

5. The vascular intervention device delivery system of claim 4 wherein the integral anchor has a T shape; and the spool defines a T shaped slot sized to receive the T shape of the integral anchor.

6. The vascular intervention device delivery system of claim 5 wherein each of three legs of the T shape is defined by two side by side segments of the pull; and two legs of the three legs are in contact with the inner surface and a third leg of the three legs extends through the wall opening in the wall.

7. The vascular intervention device delivery system of claim 1 wherein the wall opening has a centerline that intersects the axis of rotation defined by the handle.

8. The vascular intervention device delivery system of claim 7 wherein the integral anchor has a T shape that includes three legs; and two legs of the three legs are in contact with the inner surface and a third leg of the three legs extends through the wall opening in the wall.

9. The vascular intervention device delivery system of claim 8 wherein the pull includes a proximal segment integral with the distal segment;

the proximal segment includes the integral anchor; and
the proximal segment has a greater ductility than the distal segment.

10. The vascular intervention device delivery system of claim 9 wherein the pull is contact wound around the collection surface.

11. The vascular intervention device delivery system of claim 10 wherein the proximal segment is wound at least once completely around the collection surface when the retractable sheath is at the first position.

12. The vascular intervention device delivery system of claim 11 wherein each of the three legs of the T shape is defined by two side by side segments of the pull.

13. A vascular intervention device delivery system comprising:

a handle that defines a central opening with a center that defines an axis of rotation;
a thumbwheel that includes an axle received in the central opening so that the thumbwheel is rotatably mounted in the handle to rotate about the axis of rotation, and having a radially outward thumb surface and a spool;
a catheter with a proximal end attached to the handle, and a distal carrier segment for mounting a vascular intervention device thereon;
a retractable sheath movable from a first position covering the distal carrier segment to a second position retracted proximally uncovering the distal carrier segment;
a pull extending between the thumbwheel and the retractable sheath;
wherein the spool has an inner surface separated from a collection surface by a wall, and the pull extends through a wall opening in the wall and terminates at a proximal end with an integral anchor that is a deformed segment of the pull in contact with the inner surface;
the retractable sheath moving responsive to rotation of the thumbwheel in a first direction
wherein the handle includes a key shaped hub that defines the central opening, and the thumbwheel includes a ratchet surface of a ratchet;
a ratchet pawl of the ratchet being mounted in the handle and having a catch in contact with the ratchet surface, and the key shaped hub is received in a matching key shaped opening defined by the ratchet pawl; and
the ratchet locking the thumbwheel against rotation in a second direction that is opposite to the first direction.

14. The vascular intervention device delivery system of claim 13 wherein the pull is contact wound around the collection surface.

15. The vascular intervention device delivery system of claim 14 wherein the pull includes a proximal segment integral with a distal segment;

the proximal segment includes the integral anchor; and
the proximal segment has a greater ductility than the distal segment.

16. The vascular intervention device delivery system of claim 15 wherein the spool defines a slot that opens to the wall opening in the wall; and the slot has a shape that matches, and is sized to receive, a profile shape of the integral anchor.

17. The vascular intervention device delivery system of claim 16 wherein the profile shape of the integral anchor is a T shape.

18. The vascular intervention device delivery system of claim 17 wherein the proximal segment is wound at least once completely around the collection surface when the retractable sheath is at the first position.

19. The vascular intervention device delivery system of claim 18 wherein each of three legs of the T shape is defined by two side by side segments of the pull.

* * * * *